United States Patent
Kratzenberg

(10) Patent No.: US 9,949,454 B1
(45) Date of Patent: Apr. 24, 2018

(54) *BEGONIA* HYBRID '1620-8T1'

(71) Applicant: Ernst Benary Samenzucht GmbH, Hann. Münden (DE)

(72) Inventor: Sabine Kratzenberg, Hann. Münden (DE)

(73) Assignee: Ernst Benary Samenzucht GmbH, Hann. Münden (DE)

( * ) Notice: Subject to any disclaimer, the term of this patent is extended or adjusted under 35 U.S.C. 154(b) by 0 days.

(21) Appl. No.: 15/476,771

(22) Filed: Mar. 31, 2017

(51) Int. Cl.
*A01H 5/02* (2018.01)
*A01H 1/02* (2006.01)

(52) U.S. Cl.
CPC .............. *A01H 5/0238* (2013.01); *A01H 1/02* (2013.01)

(58) Field of Classification Search
None
See application file for complete search history.

(56) References Cited

PUBLICATIONS

Blooms 2009 Edition, Benary.*

* cited by examiner

*Primary Examiner* — David H Kruse
(74) *Attorney, Agent, or Firm* — Morrison and Foerster LLP

(57) ABSTRACT

A hybrid *begonia* designated '1620-8T1' is disclosed. The invention relates to the seeds of hybrid *begonia* '1620-8T1' to the plants of hybrid *begonia* '1620-8T1' and to methods for producing a hybrid plant, and to methods for producing other *begonia* lines, cultivars or hybrids derived from the hybrid *begonia* '1620-8T1'.

14 Claims, 2 Drawing Sheets
(2 of 2 Drawing Sheet(s) Filed in Color)

BEGONIA HYBRID '1620-8T1'

FIELD OF THE INVENTION

The present invention relates to the field of plant breeding. In particular, the present invention relates to a new and distinctive *begonia* interspecific hybrid (*Begonia×benariensis*) designated '1620-8T1'.

BACKGROUND OF THE INVENTION

*Begonia* is a genus of perennial flowering plants that is native to moist subtropical and tropical climates and contains more than 1,600 species and hundreds of hybrids. Depending on the climate, some *begonia* plants are grown indoors as ornamental houseplants or are cultivated outside for their bright colorful flowers. *Begonia* plants have fleshy leaves and stems, and the leaves are often magnificently colored and textured. Cultivated *begonia* plants often have showy flowers of white, pink, scarlet or yellow color.

*Begonia* plants are monoecious, with unisexual male and female flowers occurring separately on the same plant; the male contains numerous stamens and the female has a large inferior ovary and two to four branched or twisted stigmas. In most *begonia* species, the fruit is a winged capsule containing numerous minute seeds. The leaves, which are often large and variously marked or variegated, are usually asymmetric.

The American *Begonia* Society classifies begonias into eight major groups including: cane-like, shrub, rhizomatous, semperflorens (wax type), tuberous, rex, trailing-scandent, and thick stemmed. The *begonia* genus is unusual in that species throughout the genus, even those from different continents, can frequently be hybridized with each other, which has led to an enormous number of cultivars. Most begonias propagate easily by seed or from stem cuttings.

*Begonia* plants are a popular and valuable ornamental plant. Thus, there is a continued need to develop new *begonia* hybrids with unique colors.

SUMMARY OF THE INVENTION

In order to meet these needs, the present invention is directed to improved *begonia* hybrids. In one embodiment, the present invention is directed to a *begonia* interspecific hybrid, (*Begonia×benariensis*), seed designated as '1620-8T1' having ATCC Accession Number PTA-124630. In one embodiment, the present invention is directed to a *begonia* interspecific hybrid (*Begonia×benariensis*) plant and parts isolated therefrom produced by growing '1620-8T1' *begonia* seed. In another embodiment, the present invention is directed to a *begonia* interspecific hybrid (*Begonia×benariensis*) plant and parts isolated therefrom having all the physiological and morphological characteristics of a *begonia* interspecific hybrid (*Begonia×benariensis*) plant produced by growing '1620-8T1' *begonia* seed having ATCC Accession Number PTA-124630. In still another embodiment, the present invention is directed to an $F_1$ hybrid *begonia* interspecific hybrid (*Begonia×benariensis*) seed, plants grown from the seed, and fruit isolated therefrom having '1620-8T1' as a parent, where '1620-8T1' is grown from '1620-8T1' *begonia* seed having ATCC Accession Number PTA-124630.

*Begonia* plant parts include *begonia* flowers, leaves, ovules, pollen, seeds, fruits, parts of fruits, cells, and the like. In another embodiment, the present invention is further directed to *begonia* flowers, leaves, ovules, pollen, seeds, fruits, and/or parts of fruits isolated from '1620-8T1' *begonia* plants. In certain embodiments, the present invention is further directed to pollen or ovules isolated from '1620-8T1' *begonia* plants. In another embodiment, the present invention is further directed to protoplasts produced from '1620-8T1' *begonia* plants. In another embodiment, the present invention is further directed to tissue culture of '1620-8T1' *begonia* plants, and to *begonia* plants regenerated from the tissue culture, where the plant has all of the morphological and physiological characteristics of '1620-8T1' *begonia*. In certain embodiments, tissue culture of '1620-8T1' *begonia* plants is produced from a plant part selected from flower, leaf, anther, pistil, stem, petiole, root, root tip, fruit, seed, cotyledon, hypocotyl, embryo, and meristematic cell.

In yet another embodiment, the present invention is further directed to a method of selecting *begonia* plants, by a) growing '1620-8T1' *begonia* plants where the '1620-8T1' plants are grown from *begonia* seed having ATCC Accession Number PTA-124630 and b) selecting a plant from step a). In another embodiment, the present invention is further directed to *begonia* plants, plant parts and seeds produced by the *begonia* plants where the *begonia* plants are isolated by the selection method of the invention.

In another embodiment, the present invention is further directed to a method of making *begonia* seeds by crossing a *begonia* plant grown from '1620-8T1' *begonia* seed having ATCC Accession Number PTA-124630 with another *begonia* plant, and harvesting seed therefrom. In still another embodiment, the present invention is further directed to *begonia* plants, *begonia* parts from the *begonia* plants, and seeds produced therefrom where the *begonia* plant is grown from seed produced by the method of making *begonia* seed of the invention. In some embodiments, the *begonia* plant grown from *begonia* seed produced by the method of making *begonia* seed is a transgenic *begonia* plant.

In another embodiment, the present invention is further directed to a method of making *begonia* variety '1620-8T1' by selecting seeds from the cross of one '1620-8T1' plant with another '1620-8T1' plant, a sample of '1620-8T1' *begonia* seed having been deposited under ATCC Accession Number PTA-124630.

According to the invention, there is provided a hybrid *begonia* plant designated '1620-8T1'. This invention thus relates to the seeds of *begonia* hybrid '1620-8T1', to the plants of *begonia* '1620-8T1' and to methods for producing a *begonia* plant produced by crossing *begonia* hybrid '1620-8T1' with itself or another *begonia* plant, and to methods for producing a *begonia* plant containing in its genetic material one or more transgenes and to the transgenic *begonia* plants produced by that method. This invention also relates to methods for producing other *begonia* cultivars or hybrids derived from *begonia* hybrid '1620-8T1' and to the *begonia* cultivars and hybrids derived by the use of those methods. This invention further relates to *begonia* seeds and plants produced by crossing *begonia* hybrid '1620-8T1' with another *begonia* cultivar.

In another embodiment, the present invention is directed to single gene converted plants of *begonia* hybrid '1620-8T1'. The single transferred gene may preferably be a dominant or recessive allele. Preferably, the single transferred gene will confer such trait as sex determination, herbicide resistance, insect resistance, resistance for bacterial, fungal, or viral disease, improved harvest characteristics, enhanced nutritional quality, or improved agronomic quality. The single gene may be a naturally occurring *begonia* gene or a transgene introduced through genetic engineering techniques.

In another embodiment, the present invention is directed to methods for developing *begonia* plants in a *begonia* plant breeding program using plant breeding techniques including recurrent selection, backcrossing, pedigree breeding, restriction fragment length polymorphism enhanced selection, genetic marker enhanced selection and transformation. Marker loci such as restriction fragment polymorphisms or random amplified DNA have been published for many years and may be used for selection (See, Pierce et al., HortScience (1990) 25:605-615; Wehner, T., *Cucurbit Genetics Cooperative Report*, (1997) 20: 66-88; and Kennard et al., *Theorical Applied Genetics* (1994) 89:217-224). Seeds, *begonia* plants, and parts thereof produced by such breeding methods are also part of the invention.

In addition to the exemplary aspects and embodiments described above, further aspects and embodiments will become apparent by reference by study of the following descriptions.

BRIEF DESCRIPTION OF THE DRAWINGS

The patent or application file contains at least one drawing executed in color. Copies of this patent or patent application publication with color drawings will be provided by the office upon request and payment of the necessary fee.

DETAILED DESCRIPTION OF THE INVENTION

Figure 1:
FIG. 1 shows a plant and flowers of *begonia* hybrid '1620-8T1'.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include higher seed yield, improved flower color, resistance to diseases and insects, tolerance to drought and heat, and better agronomic quality.

Definitions

In the description and tables that follow, a number of terms are used. In order to provide a clear and consistent understanding of the specification and claims, including the scope to be given such terms, the following definitions are provided:

Abiotic stress. As used herein, abiotic stress relates to all non-living chemical and physical factors in the environment. Examples of abiotic stress include, but are not limited to, drought, flooding, salinity, temperature, and climate change.

Allele. The allele is any of one or more alternative forms of a gene, all of which relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotype of the $F_1$ hybrid.

Cell. Cell as used herein includes a plant cell, whether isolated, in tissue culture or incorporated in a plant or plant part.

Cotyledon. One of the first leaves of the embryo of a seed plant; typically one or more in monocotyledons, two in dicotyledons, and two or more in gymnosperms.

Essentially all the physiological and morphological characteristics. A plant having essentially all the physiological and morphological characteristics means a plant having the physiological and morphological characteristics of the recurrent parent, except for the characteristics derived from the converted gene.

F#. The "F" symbol denotes the filial generation, and the # is the generation number, such as $F_1$, $F_2$, $F_3$, etc.

Gene. As used herein, "gene" refers to a segment of nucleic acid. A gene can be introduced into a genome of a species, whether from a different species or from the same species, using transformation or various breeding methods.

Genetically Modified. Describes an organism that has received genetic material from another, or had its genetic material modified, resulting in a change in one or more of its phenotypic characteristics. Methods used to modify, introduce or delete the genetic material may include mutation breeding, backcross conversion, genetic transformation, single and multiple gene conversion, and/or direct gene transfer.

Genotype. Refers to the genetic constitution of a cell or organism.

Internode. An "internode" refers to the stem segment between nodes.

Length/Width (L/W) Ratio. This ratio is determined by dividing the average length (L) by the average width (W).

Linkage. Refers to a phenomenon wherein alleles on the same chromosome tend to segregate together more often than expected by chance if their transmission was independent.

Linkage Disequilibrium. Refers to a phenomenon wherein alleles tend to remain together in linkage groups when segregating from parents to offspring, with a greater frequency than expected from their individual frequencies.

Locus. A locus confers one or more traits such as, for example, male sterility, herbicide tolerance, insect resistance, disease resistance, waxy starch, modified fatty acid metabolism, modified phytic acid metabolism, modified carbohydrate metabolism and modified protein metabolism. The trait may be, for example, conferred by a naturally occurring gene introduced into the genome of the variety by backcrossing, a natural or induced mutation, or a transgene introduced through genetic transformation techniques. A locus may comprise one or more alleles integrated at a single chromosomal location.

Multiple Gene Converted (Conversion). Multiple gene converted (conversion) includes plants developed by a plant breeding technique called backcrossing wherein essentially all of the desired morphological and physiological characteristics of an inbred are recovered, while retaining two or more genes transferred into the inbred via crossing and backcrossing. The term can also refer to the introduction of multiple genes through genetic engineering techniques known in the art.

Plant. As used herein, the term "plant" includes reference to an immature or mature whole plant, including a plant from which seed or grain or anthers have been removed. Seed or embryo that will produce the plant is also considered to be the plant.

Plant Height. Plant height in centimeters is taken from soil surface to the tip at harvest.

Plant Parts. As used herein, the term "plant parts" (or a part thereof) includes but is not limited to protoplasts, leaves, stems, roots, root tips, anthers, pistils, seed, embryo, pollen, ovules, cotyledon, hypocotyl, pod, flower, shoot, tissue, petiole, cells, meristematic cells, and the like.

Pubescence. This refers to a covering of very fine hairs closely arranged on the leaves, stems and glumes of the plant.

Quantitative Trait Loci (QTL). As used herein, "quantitative trait loci" refers to genetic loci that control to some degree numerically representable traits that are usually continuously distributed.

Regeneration. As used herein, "regeneration" refers to the development of a plant from tissue culture.

RHS. RHS refers to the Royal Horticultural Society of England which publishes an official botanical color chart quantitatively identifying colors according to a defined numbering system. The chart may be purchased from Royal Horticulture Society Enterprise Ltd., RHS Garden; Wisley, Woking; Surrey GU236QB, UK.

Rogueing. Rogueing is the process in seed production where undesired plants are removed from a variety. The plants are removed since they differ physically from the general desired expressed characteristics of the variety. The differences can be related to size, color, maturity, leaf texture, leaf margins, growth habit, or any other characteristic that distinguishes the plant.

Single gene converted. Single gene converted or conversion plant refers to plants which are developed by a plant breeding technique called backcrossing or via genetic engineering wherein essentially all of the desired morphological and physiological characteristics of a line are recovered in addition to the single gene transferred into the line via the backcrossing technique or via genetic engineering.

Overview of the *Begonia* Hybrid Variety '1620-8T1'

Figure 2:
FIG. 2 shows flowers of *begonia* hybrid '1620-8T1'.

*Begonia* hybrid '1620-8T1' is a unique interspecific hybrid in *Begonia×benariensis* that reproduces true from seeds. *Begonia* hybrid '1620-8T1' has better branching, and produces more and bigger flowers than existing *begonia* varieties. Moreover, the male parent of *begonia* hybrid '1620-8T1' is virus-free. *Begonia* hybrid '1620-8T1' also has an extraordinary outdoor performance and it flowers in both full sun and in shade. Additionally, *begonia* hybrid '1620-8T1' continues flowering in hot and dry conditions, as well as in hot and humid conditions, and is an outstanding late season performer. *Begonia* hybrid '1620-8T1' has a growing season that includes spring and summer until first frost, and is suitable for growing in all regions where bedding plants are used. *Begonia* hybrid '1620-8T1' has outstanding performance in southern regions, such as the Southeastern United States, Southeastern Europe, and Southeastern China. FIG. 1 depicts a plant and flowers of *begonia* hybrid '1620-8T1'. FIG. 2 depicts flowers of *begonia* hybrid '1620-8T1'.

*Begonia* hybrid '1620-8T1' has shown uniformity and stability for the traits, within the limits of environmental influence for the traits. *Begonia* hybrid '1620-8T1' has been produced and tested a sufficient number of years with careful attention to uniformity of plant type. *Begonia* hybrid '1620-8T1' has been produced with continued observation for uniformity of the parental lines.

Objective Description of Hybrid *Begonia* '1620-8T1'

*Begonia* hybrid variety '1620-8T1' has the following morphologic and other characteristics:

| Classification: | |
|---|---|
| Family: | Begoniaceae |
| Botanical name: | *Begonia x benariensis* |
| Common name: | Begonia |

| Plant: | |
|---|---|
| Propagation type: | Seeds |
| Form: | Annual |
| Growth habit: | Upright |
| Branching habit: | Basal |
| Height: | 75 cm |
| Width: | 65 cm |
| Time to initiate roots: | During germination |
| Root description: | Fibrous |

| Lateral branches: | |
|---|---|
| Length: | 65 cm |
| Diameter: | 1.7 cm |
| Angle: | 30° |
| Texture: | None |
| Color: | RHS 146C |

| Leaves: | |
|---|---|
| Arrangement: | Alternate |
| Length: | 12 cm to 13 cm |
| Width: | 11 cm to 11.5 cm |
| Shape: | Stalked, asymmetrical |
| Apex: | Pointed |
| Base: | Heart-shaped |
| Margin: | Slightly dentated |
| Color of upper surface: | RHS 147A |
| Color of lower surface: | RHS 148B, partly RHS 184B |
| Texture (both upper and lower surfaces): | Both smooth |
| Venation pattern: | Reticulated |
| Venation color: | RHS 148B, partly RHS 184B |
| Glossiness: | Medium |

| Petioles: | |
|---|---|
| Length: | 2.4 cm to 2.7 cm |
| Width: | 0.6 cm |
| Color (both upper and lower surfaces): | RHS 146C |
| Texture (both upper and lower surfaces): | Lengthwise stripe on the upper side |
| Pubescence color: | RHS 146C |
| Anthocyanin color: | Absent |

| Flower buds: | |
|---|---|
| Length: | 2.2 cm to 2.5 cm |
| Diameter: | 3 cm |
| Shape: | Heart-shaped without apex |
| Color: | RHS 52B |

| Flower: | |
|---|---|
| Bloom habit: | Dichasium |
| Flower form: | Male: zygomorphic flower; female: cycle |
| Color of upper surface: | Male: RHS 48C; female: RHS 48C |
| Color of lower surface: | Male: RHS 52C; female: RHS 52C |
| Fragrance: | None |
| Inflorescence height: | 9 cm |
| Inflorescence diameter: | 18 cm |
| Flower diameter of male flower: | 5.5 cm to 6 cm (flat) |
| Flower diameter of female flower: | 6.3 cm (round) |
| Flower height of male flower: | 7 cm (flat) |
| Flower height of female flower: | 3 cm |

| Pedicels: | |
|---|---|
| Length: | Male: 2.2 cm to 2.6 cm; female: 2.2 cm to 2.6 cm |
| Diameter: | Male: 1 mm; female: 3 mm |
| Angle: | 30° |
| Texture: | Smooth |
| Color: | Male: RHS 52C; female: RHS 48B |

| Peduncles: | |
|---|---|
| Length: | 8.6 cm to 9 cm |
| Diameter: | 3 mm to 4 mm |
| Angle: | 60° variable |
| Texture: | Smooth |
| Color: | RHS 146C to reddish RHS 184D |

| Reproductive organs: | |
|---|---|
| Stamens: | Many |
| Filament color: | RHS 15A |
| Pollen: | Amount: sparse; color: non-pollen color |
| Pistil: | Curled |
| Stigma number: | 6 |
| Style color: | RHS 14A |
| Ovary: | Three-winged ovary |
| Fruit and seed set: | None |

Disease and insect resistance: Nothing specific
Comparisons to Most Similar Varieties The performance of *begonia* hybrid '1620-8T1' has been evaluated in facilities for greenhouse and outdoor trials in Hannoversch Münden, Germany, and in Watsonville, Calif., and in outdoor trials in Litchfield, Mich. *Begonia* hybrid '1620-8T1' was tested in comparison to hybrid begonias as shown in Table 1.

Table 1, column 1 shows the product, column 2 shows the number of days to start of flowering in Germany, column 3 shows the number of days to 60% flowering in Germany, column 4 shows the number of days to 90% flowering in Germany, column 5 shows the number of days to 100% flowering for trials in Germany, column 6 shows the number of days to start of flowering for trials in the United States (California and Michigan), column 7 shows the number of days to 50% flowering in the U.S. and column 8 shows the number of days to 95% flowering in the U.S.

TABLE 1

| | Germany | | | | United States | | |
|---|---|---|---|---|---|---|---|
| Product | Start to flower | 60% flower | 90% flower | 100% flower | Start to flower | 50% flower | 95% flower |
| 1620-8T1 | 122 | 130 | 133 | 135 | 79 | 84 | 91 |
| 1600-05T1 | 110 | 118 | 122 | 129 | 77 | 88 | 96 |
| 1600-08T1 | 109 | 117 | 121 | 123 | 90 | 93 | 97 |
| 1600-13T3 | 101 | 106 | 113 | 113 | 84 | 86 | 91 |
| 1610-05T2 | 106 | 115 | 119 | 125 | N/A | N/A | N/A |
| 1610-09T1 | 106 | 112 | 119 | 119 | 86 | 96 | 98 |
| 1630-05T2 | 125 | 132 | 133 | 136 | 86 | 91 | 98 |
| 1630-13T1 | 175 | 130 | 132 | 133 | 84 | 86 | 98 |
| BIG Red Green Leaf | 114 | 120 | 123 | 127 | 84 | 96 | 97 |
| BIG Rose Bronze Leaf | 112 | 121 | 127 | 128 | 85 | 95 | 96 |
| BIG Red Bronze Leaf | 114 | 122 | 129 | 131 | 91 | 96 | 100 |
| Whopper Pink Green Leaf | 122 | 128 | 130 | 131 | 85 | 88 | 93 |
| Whopper Red Green Leaf | 125 | 128 | 130 | 131 | 82 | 88 | 94 |
| Whopper Rose Bronze Leaf | 126 | 129 | 131 | 133 | 85 | 91 | 96 |
| Whopper Red Dark Leaf | 125 | 130 | 132 | 138 | 86 | 94 | 97 |

Further Embodiments

*Begonia* is an important and valuable flowering plant. Thus, a continuing goal of *begonia* plant breeders is to develop stable, attractive hybrid begonias that are agronomically sound. To accomplish this goal, the *begonia* breeder must select and develop *begonia* plants with traits that result in superior cultivars.

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer for special advertising and marketing, altered seed and commercial production practices, and new product utilization. The testing preceding release of a new cultivar should take into consideration research and development costs, as well as technical superiority of the final cultivar. For seed-propagated cultivars, it must be feasible to produce seed easily and economically.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, the overall value of the advanced breeding lines, and the number of successful cultivars produced per unit of input (e.g., per year, per dollar expended, etc.).

Promising advanced breeding lines are thoroughly tested and compared to appropriate standards in environments representative of the commercial target area(s) for at least three years. The best lines are candidates for new commercial cultivars. Those still deficient in a few traits are used as parents to produce new populations for further selection.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of *begonia* plant breeding is to develop new, unique, and superior hybrid begonias. The breeder initially selects and crosses two or more parental lines, followed by repeated selfing and selection, producing many new genetic combinations. The breeder can theoretically generate billions of different genetic combinations via crossing, selfing, and mutations. The breeder has no direct control at the cellular level. Therefore, two breeders will never develop the same line, or even very similar lines, having the same *begonia* traits.

Each year, the plant breeder selects the germplasm to advance to the next generation. This germplasm is grown under different geographical, climatic, and soil conditions, and further selections are then made during, and at the end of, the growing season. The cultivars that are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same line twice by using the exact same original parents and the same selection techniques. This unpredictability results in the expenditure of large research monies to develop superior hybrid begonias.

The development of commercial hybrid begonias requires the development of *begonia* varieties, the crossing of these varieties, and the evaluation of the crosses. Pedigree breeding and recurrent selection breeding methods are used to develop cultivars from breeding populations. Breeding programs combine desirable traits from two or more varieties or various broad-based sources into breeding pools from which cultivars are developed by selfing and selection of desired phenotypes. The new cultivars are crossed with other varieties and the hybrids from these crosses are evaluated to determine which have commercial potential.

Pedigree breeding is used commonly for the improvement of self-pollinating crops or inbred lines of cross-pollinating crops. Two parents which possess favorable, complementary traits are crossed to produce an $F_1$. An $F_2$ population is produced by selfing one or several $F_1$'s or by intercrossing two $F_1$'s (sib mating). Selection of the best individuals is usually begun in the $F_2$ population. Then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines with each generation due to failure of some seeds to germinate or some plants to produce at least one seed. As a result, not all of the $F_2$ plants originally sampled in the population will be represented by a progeny when generation advance is completed.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs—which are also referred to as Microsatellites), and Single Nucleotide Polymorphisms (SNPs).

Isozyme Electrophoresis and RFLPs have been widely used to determine genetic composition. Shoemaker and Olsen (Molecular Linkage Map of Soybean (*Glycine max*), pp. 6.131-6.138 in S. J. O'Brien (ed.) *Genetic Maps: Locus Maps of Complex Genomes*, Cold Spring Harbor Laboratory Press, Cold Spring Harbor, N.Y. (1993)) developed a molecular genetic linkage map that consisted of 25 linkage groups with about 365 RFLP, 11 RAPD, three classical markers, and four isozyme loci. See also, Shoemaker, R. C., RFLP Map of Soybean, pp. 299-309, in Phillips, R. L. and Vasil, I. K. (eds.), DNA-Based Markers in Plants, Kluwer Academic Press, Dordrecht, the Netherlands (1994).

SSR technology is currently the most efficient and practical marker technology; more marker loci can be routinely used and more alleles per marker locus can be found using SSRs in comparison to RFLPs. For example, Diwan and Cregan described a highly polymorphic microsatellite locus in soybean with as many as 26 alleles. Diwan, N. and Cregan, P. B., *Theor. Appl. Genet.*, 95:22-225 (1997). SNPs may also be used to identify the unique genetic composition of the invention and progeny varieties retaining that unique genetic composition. Various molecular marker techniques may be used in combination to enhance overall resolution.

Molecular markers, which include markers identified through the use of techniques such as Isozyme Electrophoresis, RFLPs, RAPDs, AP-PCR, DAF, SCARs, AFLPs, SSRs, and SNPs, may be used in plant breeding. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Mutation breeding is another method of introducing new traits into *begonia* varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid, or acridines. Once a desired trait is observed through mutagenesis the trait may then be incorporated into existing germplasm by traditional breeding techniques. Details of mutation breeding can be found in *Principles of Cultivar Development* by Fehr, Macmillan Publishing Company (1993).

The production of double haploids can also be used for the development of homozygous varieties in a breeding program. Double haploids are produced by the doubling of a set of chromosomes from a heterozygous plant to produce a completely homozygous individual. For example, see Wan, et al., *Theor. Appl. Genet.*, 77:889-892 (1989).

Descriptions of other breeding methods that are commonly used for different traits and crops can be found in one of several reference books (e.g., *Principles of Plant Breeding*, John Wiley and Son, pp. 115-161 (1960); Allard (1960); Simmonds (1979); Sneep, et al. (1979); Fehr (1987); "Carrots and Related Vegetable Umbelliferae," Rubatzky, V. E., et al. (1999).

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Any DNA sequences, whether from a different species or from the same species, which are introduced into the genome using transformation or various breeding methods, are referred to herein collectively as "transgenes." Over the last fifteen to twenty years, several methods for producing transgenic plants have been developed, and the present invention, in particular embodiments, also relates to transformed versions of the claimed line.

Nucleic acids or polynucleotides refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. Less common bases, such as inosine, 5-methylcytosine, 6-methyladenine, hypoxanthine, and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR, and in vitro or in vivo transcription.

Plant transformation involves the construction of an expression vector that will function in plant cells. Such a vector comprises DNA comprising a gene under control of, or operatively linked to, a regulatory element (for example, a promoter). The expression vector may contain one or more such operably linked gene/regulatory element combinations. The vector(s) may be in the form of a plasmid, and can be used alone or in combination with other plasmids, to provide transformed *begonia* plants using transformation methods as described below to incorporate transgenes into the genetic material of the *begonia* plant(s).

Gene Conversion

When the term "*begonia* plant" is used in the context of the present disclosure, this also includes any gene conversions of that variety. The term "gene converted plant" as used herein refers to those *begonia* plants which are developed by backcrossing, genetic engineering, or mutation, wherein essentially all of the desired morphological and physiological characteristics of a variety are recovered in addition to the one or more genes transferred into the variety via the backcrossing technique, genetic engineering, or mutation. Backcrossing methods can be used with the present invention to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8, 9, or more times to the recurrent parent. The parental *begonia* plant which contributes the gene for the desired characteristic is termed the "nonrecurrent" or "donor parent." This terminology refers to the fact that the nonrecurrent parent is used one time in the backcross protocol and therefore does not recur. The parental *begonia* plant to which the gene or genes from the nonrecurrent parent are transferred is known as the recurrent parent as it is used for several rounds in the backcrossing protocol. Poehlman & Sleper (1994) and Fehr (1993). In a typical backcross protocol, the original variety of interest (recurrent parent) is crossed to a second variety (nonrecurrent parent) that carries the gene of interest to be transferred. The resulting progeny from this cross are then crossed again to the recurrent parent and the process is repeated until a *begonia* plant is obtained wherein essentially all of the desired morphological and physiological characteristics of the recurrent parent are recovered in the converted plant, in addition to the transferred gene from the nonrecurrent parent.

The selection of a suitable recurrent parent is an important step for a successful backcrossing procedure. The goal of a backcross protocol is to alter or substitute a trait or characteristic in the original line. To accomplish this, a gene of the recurrent cultivar is modified or substituted with the desired gene from the nonrecurrent parent, while retaining essentially all of the rest of the desired genetic, and therefore the desired physiological and morphological characteristics of the original line. The choice of the particular nonrecurrent parent will depend on the purpose of the backcross. One of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many gene traits have been identified that are not regularly selected in the development of a new line but that can be improved by backcrossing techniques. Gene traits may or may not be transgenic. Examples of these traits include, but are not limited to, male sterility, modified fatty acid metabolism, modified carbohydrate metabolism, herbicide resistance, resistance for bacterial, fungal, or viral disease, insect resistance, enhanced nutritional quality, industrial usage, yield stability, and yield enhancement. These genes are generally inherited through the nucleus. Several of these gene traits are described in U.S. Pat. Nos. 5,777,196, 5,948, 957, and 5,969,212, the disclosures of which are specifically hereby incorporated by reference.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes." Over the last fifteen to twenty years several methods for producing transgenic plants have been developed, and the present invention, in particular embodiments, also relates to transformed versions of the claimed hybrid.

Tissue Culture

Further reproduction of the variety can occur by tissue culture and regeneration. Tissue culture of various tissues of *begonia* and regeneration of plants therefrom is well known and widely published. For example, reference may be had to Teng, et al., *HortScience*. 1992, 27: 9, 1030-1032 Teng, et al., *HortScience*. 1993, 28: 6, 669-1671, Zhang, et al., *Journal of Genetics and Breeding*. 1992, 46: 3, 287-290, Webb, et al., *Plant Cell Tissue and Organ Culture*. 1994, 38: 1, 77-79, Curtis, et al., *Journal of Experimental Botany*. 1994, 45: 279, 1441-1449, Nagata, et al., *Journal for the American Society for Horticultural Science*. 2000, 125: 6, 669-672, and Ibrahim, et al., *Plant Cell, Tissue and Organ Culture*. (1992), 28(2): 139-145. It is clear from the literature that the state of the art is such that these methods of obtaining plants are routinely used and have a very high rate of success. Thus, another aspect of this invention is to provide cells which upon growth and differentiation produce *begonia* plants having the physiological and morphological characteristics of the *begonia* hybrid '1620-8T1'.

As used herein, the term "tissue culture" indicates a composition comprising isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, and the like. Means for preparing and maintaining plant tissue culture are well known in the art. By way of example, a tissue culture comprising organs has been used to produce regenerated plants. U.S. Pat. Nos. 5,959,185; 5,973,234 and 5,977,445 describe certain techniques, the disclosures of which are incorporated herein by reference.

As it is well known in the art, tissue culture of *begonia* can be used for the in vitro regeneration of *begonia* plants. Tissues cultures of various tissues of *begonia* and regeneration of plants therefrom are well known and published. By way of example, tissue cultures, some comprising organs to be used to produce regenerated plants, have been described in Burza, et al., *Plant Breeding*. 1995, 114: 4, 341-345, Pellinen, *Angewandte Botanik*. 1997, 71: 3/4, 116-118, Kuijpers, et al., *Plant Cell Tissue and Organ Culture*. 1996, 46: 1, 81-83, Colijn-Hooymans, et al., *Plant Cell Tissue and Organ Culture*. 1994, 39: 3, 211-217, Lou, et al., *HortScience*. 1994, 29: 8, 906-909, Tabei, et al., *Breeding Science*. 1994, 44: 1, 47-51, Sarmanto, et al., *Plant Cell Tissue and Organ Culture* 31:3 185-193 (1992), Cade, et al., *Journal of the American Society for Horticultural Science* 115:4 691-696 (1990), Chee, et al., *HortScience* 25:7, 792-793 (1990), Kim, et al., HortScience 24:4 702 (1989), Punja, et al., *Plant Cell Report* 9:2 61-64 (1990). *Begonia* plants could be regenerated by somatic embryogenesis. It is clear from the literature that the state of the art is such that these methods of obtaining plants are "conventional" in the sense that they are routinely used and have a very high rate of success. Thus, another aspect of this invention is to provide cells which upon growth and differentiation produce *begonia* plants having the physiological and morphological characteristics of hybrid *begonia* '1620-8T1'.

Additional Breeding Methods

The present disclosure is also directed to methods for producing a *begonia* plant by crossing a first parent *begonia* plant with a second parent *begonia* plant wherein the first or second parent *begonia* plant is a *begonia* plant of hybrid '1620-8T1'. Further, both first and second parent *begonia* plants can come from *begonia* hybrid '1620-8T1'. Thus, any such methods using *begonia* hybrid '1620-8T1' are part of this invention: selfing, backcrosses, hybrid production, crosses to populations, and the like. All plants produced using *begonia* hybrid '1620-8T1' as at least one parent are within the scope of this invention, including those developed from cultivars derived from *begonia* hybrid '1620-8T1'. Advantageously, this *begonia* cultivar could be used in crosses with other, different, *begonia* plants to produce the first generation ($F_1$) *begonia* hybrid seeds and plants with superior characteristics. The cultivar of the invention can also be used for transformation where exogenous genes are introduced and expressed by the cultivar of the invention. Genetic variants created either through traditional breeding methods using *begonia* hybrid '1620-8T1' or through transformation of hybrid '1620-8T1' by any of a number of protocols known to those of skill in the art are intended to be within the scope of this invention.

The following describes breeding methods that may be used with *begonia* hybrid '1620-8T1' in the development of further *begonia* plants. One such embodiment is a method for developing progeny *begonia* plants in a *begonia* plant breeding program comprising: obtaining the *begonia* plant, or a part thereof, of hybrid '1620-8T1', utilizing said plant or plant part as a source of breeding material, and selecting a *begonia* hybrid '1620-8T1' progeny plant with molecular markers in common with hybrid '1620-8T1' and/or with morphological and/or physiological characteristics selected from the characteristics listed above. Breeding steps that may be used in the *begonia* plant breeding program include pedigree breeding, backcrossing, mutation breeding, and recurrent selection. In conjunction with these steps, techniques such as RFLP-enhanced selection, genetic marker enhanced selection (for example, SSR markers) and the making of double haploids may be utilized.

Another method involves producing a population of *begonia* hybrid '1620-8T1' progeny *begonia* plants, by crossing hybrid '1620-8T1' with another *begonia* plant, thereby producing a population of *begonia* plants, which, on average, derive 50% of their alleles from *begonia* hybrid '1620-8T1'. A plant of this population may be selected and repeatedly selfed or sibbed with a *begonia* plant resulting from these successive filial generations. One embodiment of this invention is the *begonia* cultivar produced by this method and that has obtained at least 50% of its alleles from *begonia* hybrid '1620-8T1'.

Additional methods include, but are not limited to, expression vectors introduced into plant tissues using a direct gene transfer method, such as microprojectile-mediated delivery, DNA injection, electroporation, and the like. More preferably, expression vectors are introduced into plant tissues by using either microprojectile-mediated delivery with a biolistic device or by using *Agrobacterium*-mediated transformation. Transformed plants obtained with the protoplasm of the invention are intended to be within the scope of this invention.

Additional methods include, without limitation, chasing selfs. Chasing selfs involves identifying inbred plants among *begonia* plants that have been grown from hybrid *begonia* seed. Once the seed is planted, the inbred plants may be identified and selected due to their decreased vigor relative to the hybrid plants that grow from the hybrid seed. By locating the inbred plants, isolating them from the rest of the plants, and self-pollinating them (i.e., "chasing selfs"), a breeder can obtain an inbred line that is identical to an inbred parent used to produce the hybrid.

Accordingly, another aspect of the present invention relates to a method for producing an inbred *begonia* variety by: planting seed of the *begonia* variety '1620-8T1'; growing plants from the seed; identifying one or more inbred *begonia* plants; controlling pollination in a manner which preserves homozygosity of the one or more inbred plants; and harvesting resultant seed from the one or more inbred plants. The step of identifying the one or more inbred *begonia* plants may further include identifying plants with decreased vigor, i.e., plants that appear less robust than plants of the *begonia* variety '1620-8T1'. *Begonia* plants capable of expressing substantially all of the physiological and morphological characteristics of the parental inbred lines of *begonia* variety '1620-8T1' include *begonia* plants obtained by chasing selfs from seed of *begonia* variety '1620-8T1'.

One of ordinary skill in the art will recognize that once a breeder has obtained inbred *begonia* plants by chasing selfs from seed of *begonia* variety '1620-8T1', the breeder can then produce new inbred plants such as by sib-pollinating, or by crossing one of the identified inbred *begonia* plant with a plant of the *begonia* variety '1620-8T1'.

One of ordinary skill in the art of plant breeding would know how to evaluate the traits of two plant varieties to determine if there is no significant difference between the two traits expressed by those varieties. For example, see Fehr and Walt, *Principles of Cultivar Development*, pp. 261-286 (1987). Thus the invention includes *begonia* hybrid '1620-8T1' progeny *begonia* plants comprising a combination of at least two hybrid '1620-8T1' traits selected from the group consisting of those listed above or the hybrid '1620-8T1' combination of traits listed in the Summary of the Invention, so that said progeny *begonia* plant is not significantly different for said traits than *begonia* hybrid '1620-8T1' as determined at the 5% significance level when grown in the same environmental conditions. Using techniques described herein, molecular markers may be used to identify said progeny plant as a *begonia* hybrid '1620-8T1' progeny plant. Mean trait values may be used to determine whether trait differences are significant, and preferably the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme environmental conditions.

Progeny of *begonia* hybrid '1620-8T1' may also be characterized through their filial relationship with *begonia* hybrid '1620-8T1', as for example, being within a certain number of breeding crosses of *begonia* hybrid '1620-8T1'. A breeding cross is a cross made to introduce new genetics into the progeny, and is distinguished from a cross, such as a self or a sib cross, made to select among existing genetic alleles. The lower the number of breeding crosses in the pedigree, the closer the relationship between *begonia* hybrid '1620-8T1' and its progeny. For example, progeny produced by the methods described herein may be within 1, 2, 3, 4, or 5 breeding crosses of *begonia* hybrid '1620-8T1'.

As used herein, the term "plant" includes plant cells, plant protoplasts, plant cell tissue cultures from which *begonia* plants can be regenerated, plant calli, plant clumps and plant cells that are intact in plants or parts of plants, such as fruit, leaves, pollen, embryos, cotyledons, hypocotyl, roots, root tips, anthers, pistils, flowers, seeds, stems and the like.

The use of the terms "a," "an," and "the," and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While a number of exemplary aspects and embodiments have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope.

DEPOSIT INFORMATION

A deposit of the hybrid *begonia* '1620-8T1' is maintained by Ernst Benary Samenzucht GmbH, having an address at Friedrich-Benary-Weg 1, 34346 Hann. Münden, Germany. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 2,500 seeds of the same variety made according to the Budapest Treaty in the American Type Culture Collection, (ATCC), ATCC Patent Depository, 10801 University Boulevard, Manassas, Va., 20110, USA.

At least 2500 seeds of hybrid *begonia* '1620-8T1' were deposited on Nov. 22, 2017 according to the Budapest Treaty in the American Type Culture Collection (ATCC), ATCC Patent Depository, 10801 University Boulevard, Manassas, Va., 20110, USA. The deposit has been assigned ATCC number PTA-124630. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed.

The deposit will be maintained in the ATCC depository, which is a public depository, for a period of at least 30 years, or at least 5 years after the most recent request for a sample of the deposit, or for the effective life of the patent, whichever is longer, and will be replaced if a deposit becomes nonviable during that period.

The invention claimed is:

1. Hybrid *Begonia* seed designated as '1620-8T1', representative sample of seed having been deposited under ATCC Accession Number PTA-124630.

2. A *Begonia* plant produced by growing the seed of claim 1.

3. A plant part from the plant of claim 2.

4. The plant part of claim 3, wherein said part is a flower, a leaf, or a cell.

5. The plant part of claim 4, wherein said part is a flower.

6. A *Begonia* plant having all the physiological and morphological characteristics of the *Begonia* plant of claim 2.

7. A plant part from the plant of claim 6.

8. The plant part of claim 7, wherein said part is a flower, a leaf, or a cell.

9. The plant part of claim 8, wherein said part is a flower.

10. Pollen or an ovule of the plant of claim 2.

11. A protoplast produced from the plant of claim 2.

12. A tissue culture produced from protoplasts or cells from the plant of claim 2, wherein said cells or protoplasts are produced from a plant part selected from the group consisting of leaf, anther, pistil, stem, petiole, root, root tip, flower, cotyledon, hypocotyl, embryo and meristematic cell.

13. A *Begonia* plant regenerated from the tissue culture of claim 12, wherein the plant has all of the morphological and physiological characteristics of a *Begonia* plant produced by growing hybrid *Begonia* seed designated as '1620-8T1', representative sample of seed having been deposited under ATCC Accession Number PTA-124630.

14. A method of making *Begonia* seeds, said method comprising crossing the plant of claim 2 with another *Begonia* plant and harvesting seed therefrom.

* * * * *